United States Patent

Morgantini et al.

[11] Patent Number: 5,800,776
[45] Date of Patent: Sep. 1, 1998

[54] METHOD AND A MACHINE FOR STERILIZING OR DISINFECTING WASTE

[75] Inventors: Gianpiero Morgantini; Roberto Pellegrin, both of Turin, Italy

[73] Assignee: S.T.R.A.P. SrL, Turin, Italy

[21] Appl. No.: 583,058

[22] PCT Filed: Jul. 18, 1994

[86] PCT No.: PCT/EP94/02357

§ 371 Date: Mar. 18, 1996

§ 102(e) Date: Mar. 18, 1996

[87] PCT Pub. No.: WO95/03072

PCT Pub. Date: Feb. 2, 1995

[30] Foreign Application Priority Data

Jul. 21, 1993 [IT] Italy .................. TO93 A 000547

[51] Int. Cl.⁶ .................................................. A61L 2/00
[52] U.S. Cl. .................. 422/1; 241/606; 241/DIG. 38; 366/144; 366/302; 422/28; 422/38; 422/307; 422/309
[58] Field of Search .................. 422/1, 28, 32, 422/38, 307, 309; 366/144, 147, 22, 24, 277, 302; 241/606, DIG. 38, 23, 65, 66

[56] References Cited

U.S. PATENT DOCUMENTS

| | | | |
|---|---|---|---|
| 3,885,057 | 5/1975 | Wander et al. | 426/519 |
| 4,331,070 | 5/1982 | Denk | 99/483 |
| 4,446,781 | 5/1984 | Schmitt | 99/483 |
| 4,552,720 | 11/1985 | Baker, Sr. et al. | 422/26 |
| 5,217,688 | 6/1993 | Von Lersner | 422/309 X |
| 5,254,265 | 10/1993 | Chung et al. | 210/774 |
| 5,397,535 | 3/1995 | Kaneko | 422/309 X |

FOREIGN PATENT DOCUMENTS

| | | |
|---|---|---|
| 0383553 | 8/1990 | European Pat. Off. |
| 9208697 | 10/1992 | Germany. |
| WO9212738 | 6/1992 | WIPO. |

*Primary Examiner*—Krisanne Thornton
*Attorney, Agent, or Firm*—Sughrue, Mion, Zinn, Macpeak & Seas, PLLC

[57] ABSTRACT

A method for heat sterilizing or disinfecting hospital waste includes the steps of grinding and/or comminuting the waste under a cutting force and for an amount of time such that a quantity of heat which is sufficient to reach and maintain the sterilization or disinfection temperature within the massive waste is generated by friction. The apparatus includes a rotor provided with vanes or blades for grinding or comminuting the waste and a plurality of fixed strikers in the form of vanes or blades associated with the walls of the housing.

11 Claims, 1 Drawing Sheet

METHOD AND A MACHINE FOR STERILIZING OR DISINFECTING WASTE

BACKGROUND OF THE INVENTION

The present invention relates to a method and a machine for sterilizing or disinfecting waste, particularly infected hospital waste, based on the known method of the thermal decomposition of the proteins constituting living cells.

In the known methods of heat-sterilization or disinfection, the difficulty of heating the material to be treated involves cycles of long duration, caused by the low coefficient of transfer of heat from the exterior to the interior of the waste. In these methods, heat is transferred to the ready-ground waste or by blowing in saturated steam at a pressure of approximately 0.5 Pascal, if autoclave systems are used, or by blowing in hot air or steam superheated to a temperature of approximately 180° C. in dry systems, or even by heating through the walls.

Although systems exist which use micro-wave radiation to make the heat penetrate the interior of the waste, the plants using this principle can only attain the temperatures necessary for sterilization with difficulty since the need for the presence of water for transforming the microwaves into heat energy prevents the temperature being increased to above the boiling temperature of the water.

SUMMARY OF THE INVENTION

The object of the present invention is to provide an improved method and apparatus which enable waste to be sterilized without contamination risks and which, following the treatment, give rise to an easily disposable sterilized material.

A further object of the invention is to provide a method and an apparatus suitable to be used for the disposal of infected waste, in the hospital environment, even on a small scale, relatively economically and suitable for automation.

In order to attain these objects, the method which is the subject of the invention is characterized in that it comprises the operation of grinding and/or comminuting the waste under a shear stress and for an amount of time such that a quantity of heat sufficient to reach and maintain the sterilization or disinfection temperature in the mass of waste is generated by friction.

The distinctiveness of the method according to the invention is that the heat energy necessary for reaching and maintaining the temperature is generated by impact as well as by both intra- and extra-molecular friction, making use of the kinetic energy supplied to the system by a bladed shaft rotating at high speed inside a housing, preferably provided with fixed striker plates. This system enables the programmed temperature to be reached particularly quickly and the latter is then checked, preferably by the dosing and evaporation of water. In addition to the sterilization (or disinfection) treatment, the method also enables the waste to be comminuted, the plastics material present in, or suitably added to, the waste to be melted, and the treated material finally to be granulated.

The apparatus which is the subject of the invention is characterized in that it comprises a housing suitable for containing waste, a rotor inside the housing provided with vanes or blades suitable for grinding and/or comminuting the waste, and drive means which can rotate the rotor at a speed such that a temperature sufficient for the sterilization or disinfection of the waste is generated by friction and maintained inside this housing, and water intake means in the housing.

The value of the temperature in the bulk of waste, inside the housing, is determined according to whether the intention is simply disinfection and thus simply destroying the pathogenic micro-organisms, or is complete sterilization and thus complete removal of the living sporogenous or asporogenous micro-organisms.

After having reached in a few minutes the programmed temperature at which the plastics parts present or added, as it will be stated hereinafter, soften ,such temperature is maintained for approximately half an hour, dissipating the heat derived from energetic agitation by means of the injection of water. The dosing of the water is controlled by a temperature regulator; this dosing also enables a high moisture content to be maintained locally, which, as stated in the literature, facilitates the decomposition of the proteins.

The fumes which are released by the system are passed into an electrical sterilizer with a high temperature (approximately 800° C.) before being dissolved in a water absorber.

The coefficient of friction of the mass of waste to be treated can be increased by the addition of thermoplastics material such as polyethylene, polypropylene, etc., preferably of the coloured type so as to give the treated material a specific colour.

The addition of further thermoplastics materials besides those normally present in the waste enables the maximum temperature which can be reached by friction in the mass to be considerably increased—to more than 250° C.—and thus for the duration of the time for which the temperature is maintained in the mass itself to be reduced.

The melting of the plastics material and subsequent solidification by cooling and dosing of water enable a treated material to be obtained which is completely homogeneous both with respect to its colouring and its composition.

At the end of the period during which the temperature is maintained, the mass is cooled by increasing the dosing of water and also by suitably decreasing the speed of the rotor and by circulating air or water on the jacket of the apparatus or by placing the apparatus under a slight vacuum.

At the end of the cycle, the sterilized or disinfected waste is in the granulated and cooled form and can be discharged without emitting fumes, vapours or odours.

BRIEF DESCRIPTION OF THE DRAWINGS

Further advantages and characteristics of the method and apparatus according to the invention will become clear from the following detailed description given with reference to the appended drawing, provided purely by way of non-limiting example in which an apparatus for performing the method is shown schematically.

DETAILED DESCRIPTION OF THE INVENTION

Figure 1:
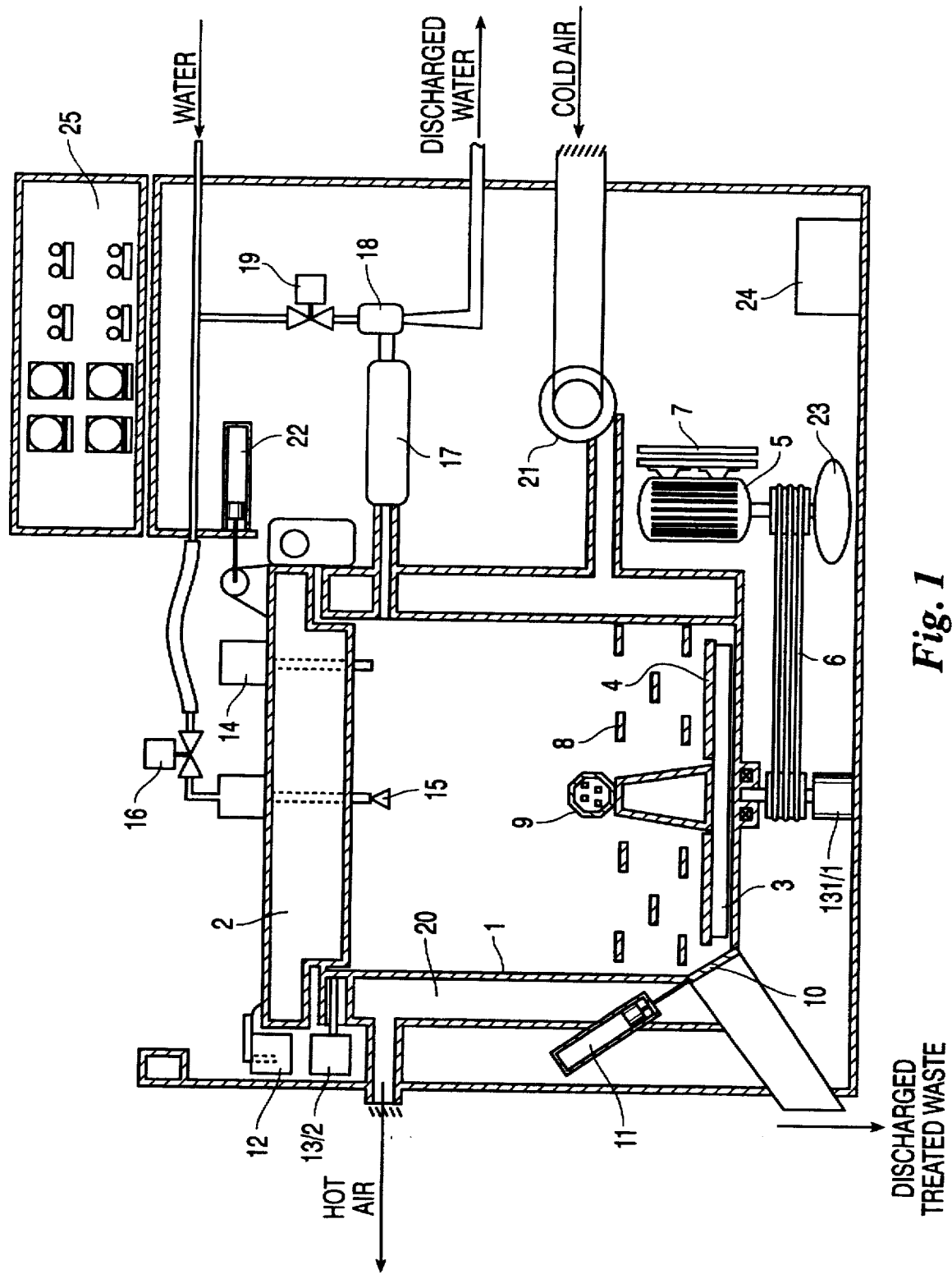

The waste is loaded into a housing defining a chamber (1) of strong sheet metal with sides protected by anti-wear shields, preferably made of manganese steel. The chamber is closed by a cover (2) manually or hydraulically actuated by means of a cylinder (22) and a hydraulic unit (24). Inside the chamber, a vaned rotor (3), with highly resistant replaceable steel blades (4), is rotated at high speed, for example at 1500 rpm. The rotor is actuated by a powerful electric motor (5) and a system of belts and pulleys (6) tensioned by a belt tightener (7). A hydraulic coupling (23) for reducing absorption on starting and for compensating the forces owing to breakdowns or overloading can be mounted on the large-scale machines.

As an alternative to the electrical system, actuation can be achieved by a hydraulic motor and an oleodynamic unit.

Preferably, sturdy, stationary, steel striker plates 8, of which the purpose is to strike, crush and restrain the material such that the kinetic energy can be converted into heat energy, are mounted in the lower part of the chamber.

Preferably, the rotary shaft carries a central mounting suitable for receiving a test-tube carrier (9) with holes which can be opened and charged with samples of particular spores or bacteria (such as, for example, *Bacillus stearothermophilus* or *Bacillus subtilis*) such that the correct functioning of the sterilizing or disinfecting machine can be checked periodically in a suitable test cycle.

At the end of the cycle, the material is discharged by the opening of a shutter (10), by means of a hydraulic system (11) or another motorized device.

The apparatus is provided with safety devices to protect against accidents, and in particular with a microswitch device (12) which prevents the rotor starting if the cover is not closed, and a hydraulic device consisting of an automatic pump (13/1) and of a piston (13/2) which prevent the cover opening when the rotor is rotating.

The temperature inside the chamber is measured and controlled by an indicator—regulator (14), the sensitive bulb of which can be installed on the cover but preferably inside a stationary vane which actuates the opening of a solenoid valve (16) and the injection of water from a nozzle (15) in specific stages of the program. The emissions which are released during the treatment cycle pass into a small furnace (17) in which a high temperature (approximately 800° C.) is achieved by electrical resistances such that these emissions are sterilized.

After passing through the furnace, the emissions are absorbed in a water absorber with a nozzle (18) which is actuated by a solenoid valve (19).

At the end of the step during which the temperature is maintained, the treated material is cooled by slowing down the speed of the rotor, by the dosing of the water, by placing the housing under a slight vacuum, by increasing the water at the nozzle (18), and by circulating air in a space (20) surrounding the housing, by means of a fan (21), or water driven by a motorized valve.

The apparatus is completed by a hydraulic unit (24) for actuating the service pistons and valves, as well as an electric control panel (25).

EXAMPLE 1

Apparatus provided with a chamber which is 600 mm in diameter and 800 mm high is equipped with a coaxial, bladed rotor rotating at 750–1500 rpm and consisting of two blade-carrying vanes connected to a 50 kW electric motor.

Anti-wear shields and six stationary blades are disposed along the lower circumference of the chamber.

30 kg of infected hospital waste and 7 kg of a coloured polythenic master are introduced into the chamber and the cover is closed. The machine is started according to a programmed cycle in which a temperature of 160° C. is reached and maintained. The temperature is reached in 5 minutes, after which the water regulating and injecting system comes into action and maintains the temperature at this level for approximately 30 minutes. At the end of this step, the speed of the rotor automatically drops to 750 rpm and the dosing of the water decreases the temperature to 80° C. in 2 minutes. The cooling step is started by air being blown onto the jacket for 10 minutes; thereafter, the temperature of the material is 60° C., the opening of the shutter causes the granulated and sterilized material to be discharged automatically in approximately 1 minute. The machine then stops and is ready to perform a new cycle.

EXAMPLE 2

Apparatus provided with a chamber which is 1200 mm in diameter and 800 mm high is equipped with a coaxial, bladed rotor rotating at between 0 and 1500 rpm and consisting of two blade-carrying vanes connected to a 250 kW hydraulic motor.

Anti-wear shields and 25 stationary blades are disposed along the lower circumference of the chamber.

120 kg of infected hospital waste and 30 kg of coloured polypropylenic master are introduced into the chamber and the cover is closed.

The machine is started according to a programmed cycle of which the first step is to reach a temperature of 150° C. This temperature is reached in 10 minutes, whereupon the water regulating and injection system comes into action and maintains the temperature at this level for 20 minutes. At the end of this step, the dosing of water is automatically suspended since the second step of the cycle program provides for the further heating of the mass to a temperature of 180° C. which is reached in 1 minute. The speed of the rotor then drops automatically to 500 rpm and the dosing of water decreases the temperature to 80° C. in 1 minute. The cooling step is started under a vacuum and by air being blown onto the jacket for 10 minutes, after which the temperature of the material is 50° C. The opening of the shutter causes the granulated and sterilized material to be discharged automatically in approximately 2 minutes. The machine then stops and is ready to perform a new cycle.

In a further embodiment of the invention, a concentrated sodium hypochlorite acqueous solution is injected onto the mass of waste, within the housing during the sterilization cycle. Thus the water, which is sprayed and dosed, during the cycle, may advantageously be in solution with sodium hypochlorite, preferably at a concentration of 12–15% wt. active chlorine.

It has been found that the concentrated sodium hypochlorite solution, at the high temperature reached within the housing, reacts with carbon dioxide to form undissociated hypochlorous acid which in turn dissociates to gaseous Chlorine monoxide ($Cl_2O$) which is an effective chlorinating and biocidal agent.

In this embodiment the waste material being comminuted is sprayed with the concentrated NaClO solution when heated to a temperature higher than 150° C. and air, including Carbon dioxide, is introduced within the housing. The amount of $CO_2$ inherently present in the air is sufficient to cause chlorine monoxide evolution, which under the strong stirring conditions penetrates within the bulk of the waste being treated and flows through the apparatus thus improving the sterilization effect.

Residual amounts of chlorine monoxide, still present at the end of the treatment, if any, may be absorbed in the water absorber to give acqueous hypochlorous acid.

Thus, not only the waste is further sterilized, but also the emissions formed during the treatment and the internal surfaces of the apparatus. In this embodiment there is no need for feeding the emissions to furnace (17) prior to feeding them to the water absorber.

Naturally, the principle of the invention remaining the same, the forms of embodiment and details of description can be varied widely with respect to what has been described and illustrated above purely by way of non-limiting example.

What is claimed is:

1. A method for the heat-sterilization or disinfection of infected hospital waste, comprising the step of grinding and/or comminuting the waste at a temperature suitable for heat-sterilization and/or disinfection, wherein said grinding and/or comminuting step is carried out under a shear stress and for an amount of time such as to generate, solely by friction, an amount of heat sufficient for attaining and maintaining said sterilization or disinfection temperature within the mass of waste, in the absence of direct or indirect additional heat supply and dissipating frictional heat by dosing liquid water onto the waste being comminuted when the sterilization and/or disinfection temperature is reached thereby to control the sterilization and/or disinfection temperature.

2. A method according to claim 1, wherein the dosed liquid water is in solution with sodium hypochlorite.

3. A method according to claim 1, wherein the sterilization and/or disinfection temperature attained by frictional heat is at least 150° C.

4. A method according to claim 1, in which the heat is generated in the mass of waste by friction and shear, making use of the kinetic energy transmitted by a rotor provided with vanes or blades and rotating at a high speed.

5. A method according to claim 4, in which the rotor cooperates with a plurality of stationary strikers in the form of vanes or blades for accelerating the conversion of kinetic energy into heat.

6. A method according to claim 1, in which a plastics material master, polyethylene or polypropylene, is added to the waste to be treated.

7. Method according to claim 6, wherein the temperature attained by frictional heat is sufficient to cause softening and/or melting of said plastics material.

8. A method according to claim 1, wherein a concentrated sodium hypochlorite aqueous solution is fed onto the waste.

9. A method according to claim 1, wherein the sterilized comminuted waste is finally cooled by adding water onto the heated waste and allowing the added water to evaporate.

10. An apparatus for heat sterilization or disinfection of waste, wherein it comprises:

a housing suitable for containing waste;

a rotor, inside the housing, provided with vanes or blades which can grind or comminute the waste;

a plurality of fixed strikers in the form of vanes or blades, on the walls of the housing;

drive means which can rotate the rotor at a speed such that a temperature sufficient for sterilizing or disinfecting the waste is generated solely by friction and maintained inside the housing; and means for injecting water into the housing to control and regulate the disinfection and/or sterilization temperature.

11. An apparatus according to claim 10, wherein the apparatus further comprises vent means associated with the walls of the housing for extracting the fumes generated during the sterilization and/or disinfection treatment, a sterilizer device adapted to receive the emitted fumes and heat such fumes to a sterilization temperature, and absorbent means communicating with the sterilizer, adapted to receive and absorb such fumes.

* * * * *